United States Patent [19]

Schmerling et al.

[11] 4,039,564

[45] Aug. 2, 1977

[54] PRODUCTION OF CARBOXYLIC ACIDS FROM UNSATURATED HYDROCARBONS IN THE PRESENCE OF HF AND A CUPROUS COMPOUND

[75] Inventors: Louis Schmerling, Riverside; Joseph Levy, Northbrook, both of Ill.

[73] Assignee: UOP Inc., Des Plaines, Ill.

[21] Appl. No.: 652,275

[22] Filed: Jan. 26, 1976

Related U.S. Application Data

[63] Continuation-in-part of Ser. No. 458,640, April 8, 1974, abandoned.

[51] Int. Cl.$^2$ .............................................. C07C 51/14
[52] U.S. Cl. ............................... 260/413; 260/514 M; 260/533 A
[58] Field of Search ................ 260/413, 533 A, 514 M

[56] References Cited

U.S. PATENT DOCUMENTS

| | | | |
|---|---|---|---|
| 1,924,767 | 8/1933 | Carpenter | 260/533 A |
| 2,022,244 | 11/1935 | Larson | 260/533 A |
| 2,831,877 | 4/1958 | Koch | 260/413 |
| 3,661,951 | 5/1972 | Miller, Jr. et al. | 260/413 |
| 3,910,963 | 10/1975 | Souma et al. | 260/413 |

OTHER PUBLICATIONS

The Canadian Patent Office Record & Register of Copyrights and Trademarks, vol. LXII, No. 11, Mar. 13, 1934, p. 561, No. 339,934–Carpente G. B.

*Primary Examiner*—Winston A. Douglas
*Assistant Examiner*—P. E. Konopka
*Attorney, Agent, or Firm*—James R. Hoatson, Jr.; Raymond H. Nelson; William H. Page, II

[57] ABSTRACT

The desired yields of carboxylic acids which are obtained by reacting an unsaturated hydrocarbon with water and carbon monoxide in the presence of a catalyst comprising hydrogen fluoride is improved by utilizing the presence of a promoter comprising a cuprous-containing compound in the reaction mixture.

10 Claims, No Drawings

PRODUCTION OF CARBOXYLIC ACIDS FROM UNSATURATED HYDROCARBONS IN THE PRESENCE OF HF AND A CUPROUS COMPOUND

CROSS-REFERENCE TO RELATED APPLICATION

This application is a continuation-in-part of our co-pending application Ser. No. 458,640 filed Apr. 8, 1974, now abandoned all teachings of which are incorporated herein by reference thereto.

BACKGROUND OF THE INVENTION

Various processes which are directed to the production of carboxylic acids are well known in the art of chemistry. For example, one such process comprises the production of monocarboxylic acids from straight or branched chain monoolefins by the reaction of carbon monoxide and a stoichiometric amount of water in the presence of hydrogen fluoride. A prior art reference, namely, U.S. Pat. No. 2,831,877, discloses this process. However, this reference also discloses that, if so desired, boron fluoride or concentrated sulfuric acid may be added to the reaction mixture. In addition, the reference also teaches that it is advantageous to work under superatmospheric pressures which need not exceed 100 atmospheres and that pressures ranging from 20 to 50 atmospheres (294–735 psi) are advantageous. Another reference, namely, U.S. Pat. No. 3,661,951 also discloses a process for the carboxylation of olefins using a liquid hydrogen fluoride as a catalyst in which the olefinic hydrocarbons are gradually added to an initial mixture of carbon monoxide, water and from about 10 to about 40 moles of hydrogen fluoride per mole of olefin. In addition to these two references, other United States patents such as U.S. Pat. No. 1,924,767 discloses the reaction of an olefin, and usually a gaseous olefin, with carbon monoxide and steam in the presence of hydrogen bromide or hydrogen chloride and a halide of a metal such as the alkali metal or alkaline earth metals as well as copper, magnesium, strontium, barium, tin, iron, cobalt, nickel, bismuth, manganese, lead, tellurium, zinc and cadmium. In addition to those prior art references, U.S. Pat. No. 2,022,244 discloses a process for the synthesis of organic aliphatic acids in which an olefin, carbon monoxide and water are reacted in the presence of ammoniacal or acid copper solutions such as cuprous ammonium formate, cuprous phosphate, cuprous chloride and an acid such as hydrochloric acid. However, this reference does not disclose the use of the catalyst of the present invention. In addition to the catalyst such as hydrogen chloride (hydrochloric acid) and cuprous salts, the reference also discloses that calcium, zinc, sodium and potassium may be used with equivalent results. This reference also discloses that pressures ranging from 25 to 900 atmospheres (367.5 to 13,230 psi) are employed.

In like manner, an article in the *Journal of Organic Chemistry*, Volume 38, page 2016, (1973), has disclosed that tertiary carboxylic acids are synthesized by reacting olefins with carbon monoxide in the presence of concentrated sulfuric acid as a catalyst and cuprous carbonyl, which has been prepared by the reaction of cuprous oxide with carbon monoxide in the presence of the sulfuric acid catalyst.

However, none of the references disclose the use of hydrogen fluoride as a catalyst for the carboxylation of olefinic hydrocarbons with water and carbon monoxide in the presence of a cuprous compound as a promoter for the reaction. It is a well-established principle in the art of chemistry that catalysis is unpredictable. In view of the unpredictability of various catalysts, it was unexpected to find that the yields of carboxylic acids could be improved by utilizing hydrogen fluoride as a catalyst in the presence of a cuprous compound as a promoter. Now, it was also unexpected to discover that by utilizing this combination of catalyst and promoter, it was possible to effect the carboxylation of the olefinic hydrocarbon with carbon monoxide and water at relatively low pressures inasmuch as all of the previous processes operate under reaction conditions including relatively high temperatures and relatively high pressures which would make their commercial use difficult due to the corrosive and hazardous nature of hydrogen fluoride which requires costly installations and extremely difficult operating procedures.

In view of the prior art references, it was totally unexpected that, since none of the practitioners who were skilled in the art had established the feasibility of conducting the carboxylation of olefins with carbon monoxide and water in the presence of the catalyst and promoter of the present invention under the relatively mild conditions of temperature and pressure to obtain the results hereinafter set forth in greater detail, the production of carboxylic acids could be effected according to the process hereinafter set forth to afford greater yields of the desired product. Furthermore, the work with hydrogen chloride is not pertinent in view of the fact that it is well known that hydrogen chloride and hydrogen fluoride are at wide variance in their reactions with organic compounds and their ability to act as catalysts in various reactions. For example, hydrogen fluoride will catalyze the alkylation of aromatic compounds with olefins and the hydroxylation of aromatic hydrocarbons with hydrogen peroxide whereas, in contradistinction to this, hydrogen chloride is ineffective as a catalyst in either of these reactions except under extreme conditions of temperature and pressure.

This invention relates to a process for the production of carboxylic acids. More specifically, the invention relates to a process for the production of carboxylic acids which comprises reacting an unsaturated hydrocarbon with a predetermined quantity of water and carbon monoxide in the presence of a catalyst comprising hydrogen fluoride and a promoter comprising a cuprous-containing compound.

As hereinbefore set forth, it is known in the art that an unsaturated compound such as an olefin may be treated with carbon monoxide and water in the presence of hydrogen fluoride and that the pressure of the reaction system will determine the type and quantity of carboxylic acid which is produced. It has been found that when higher pressures are utilized to effect the reaction, a larger amount of "iso" acids will be produced and conversely, when lower pressures are employed, a larger quantity of "neo" acids are produced. It is, therefore, desirable in the production of carboxylic acids from olefins by treatment with carbon monoxide and water in the presence of a hydrogen fluoride catalyst to control the pressure whereby the desired acid, either iso or neo in configuration, will comprise a major portion of the desired product.

It has now been discovered that by effecting the treatment of an unsaturated hydrocarbon with a predetermined stoichiometric quantity of water and carbon monoxide in the presence of a catalyst comprising hydrogen fluoride by utilizing the presence of a promoter comprising a cuprous-containing compound, it is possible to utilize relatively mild operating conditions of temperature and pressure. The presence of the cuprous-containing promoter will enable a greater control of the desired pressure by the manufacturer in order that he may produce more specifically predominantly neo acids from the basic branched and straight-chained unsaturated hydrocarbons. It will be hereinafter shown that the promoter comprising a cuprous-containing compound will permit the production of the carboxylic acids at a substantially lower pressure than would have normally been considered possible until this time. The utilization of this invention will result in a savings to the manufacturer and an eventual savings to the consumer as a result of the decrease in the quantity of carbon monoxide necessary to afford the required pressure for the carboxylation. The utilization of the above set forth invention will also result in a decrease of the cost of production of the final product as a consequence of the lower cost of capitalization for equipment which will not be exposed to severe pressure.

The desired products of the process of this invention, namely, carboxylic acids, are utilized in the chemical industry in many ways. For example, carboxylic acids are used in the rubber industry; as an antiseptic; as a fungicide; in perfumes; as a tanning agent; as a deliming agent; for the preparation of butter; in the preparation of certain pharmaceuticals; in water purification; as an emulsifying agent; and as a sweetening agent for gasoline. For example, nonanoic acid may be utilized as a lacquer; as a plastic; in hydrotropic salt production; in the synthesis of flavors and odors; and as a vinyl plasticizer.

It is therefore an object of this invention to provide a process for the preparation of carboxylic acids.

A further object of this invention is to provide a process for the preparation of carboxylic acids utilizing certain promoter compositions of matter which will permit the production and recovery of the desired carboxylic acid in a more expedient manner.

In one aspect an embodiment of this invention resides in a process for the production of a carboxylic acid which comprises reacting a monoolefinic or diolefinic hydrocarbon with water and carbon monoxide in contact with a hydrogen fluoride catalyst, the improvement which comprises effecting the reaction in the presence of a promoter consisting of a cuprous compound.

A specific embodiment of this invention resides in a process for preparing a carboxylic acid which comprises reacting 7-tetradecene with carbon monoxide and a stoichiometric excess of water in a range of from about 1.05 to about 10 moles of water per mole of 7-tetradecene in the presence of hydrogen fluoride and a promoter comprising cuprous oxide at a temperature in the range of from about 25° to about 30° C. and a pressure in the range of from about 25 to about 85 psi, and recovering the resultant pentadecanoic acid.

Other objects and embodiments will be found in the following further detailed description of the present invention.

As hereinbefore set forth the present invention is concerned with a process for preparing carboxylic acids which comprises the treatment of an unsaturated hydrocarbon such as a monoolefinic or diolefinic hydrocarbon with a predetermined stoichiometric quantity of water and carbon monoxide in the presence of a catalyst comprising hydrogen fluoride, said process being improved by effecting the reaction in the presence of a promoter comprising a cuprous-containing compound. The use of the cuprous-containing compound as a promoter for the reaction has unexpectedly resulted in being able to effect the process at a pressure which is lower than that previously taught in the prior art and, in addition, has enabled the product to be obtained in a greater yield than has hereinbefore been obtained in the absence of any added promoter at these low pressures. The reaction is effected under reaction condition parameters which include a temperature in the range of from about $-10°$ to about 50° C. and preferably in a range of from about 0° to about 40' C., and a pressure ranging from atmospheric up to about 500 pounds per square inch (psi) or more, preferably in a range of from about 25 to about 85 psi. When superatmospheric pressures are employed, the pressures are afforded by the introduction of carbon monoxide to the reaction system for a period of time sufficient to enable the pressure in the reaction vessel or reaction zone to stabilize. The reason for the unstability of the pressure is the presence of the promoter comprising a cuprous-containing compound of the type hereinafter set forth in greater detail which will absorb the carbon monoxide by reacting with it; this reaction product between the cuprous-containing compound and the carbon monoxide being the true promoter. In addition, it is also contemplated within the scope of this invention that any inert gas such as nitrogen may also be used, if so desired, to increase the pressure in the reaction vessel or reaction zone, the total pressure of said zone or reactor being the total of the partial pressure of the carbon monoxide and the partial pressure of the substantially inert gas.

As hereinbefore stated, water is present in a stoichiometric excess over the amount of unsaturated hydrocarbon used. The molar ratio between the water and the unsaturated hydrocarbon is such that the water is present in a range of from about 1.05 moles of water to about 10 moles of water per mole of the unsaturated hydrocarbon. The optimum preferred ranges of the stoichiometric excess of water are from about 1.05 moles of water to about 2.00 moles of water per mole of the unsaturated hydrocarbon. Large excess of water has the disadvantage that it dilutes the hydrogen fluoride making it a less active catalyst. It is also considered within the scope of this invention to omit the added water. When water is omitted, the reaction products consist of acyl fluorides instead of acids. Such fluorides may be desirable end products. Alternatively, they may be hydrolyzed by reaction with hot water or aqueous alkali to yield the carboxylic acid which is otherwise formed during the reaction with the carbon monoxide and the added water.

The molar ratio of the hydrogen fluoride catalyst and the unsaturated hydrocarbon may also vary widely. In order to insure a sufficiently high rate of reaction, this ratio must, as a rule, be chosen to be not lower than 2 moles of hydrogen fluoride per mole of the unsaturated hydrocarbon and for economic reasons not higher than 50 moles of hydrogen fluoride per mole of the unsaturated hydrocarbon, the molar ratio of hydrogen fluoride catalyst to the unsaturated hydrocarbon being from about 8 moles of hydrogen fluoride to about 25 moles or more of hydrogen fluoride per mole of the unsaturated hydrocarbon.

Examples of suitable mixtures of unsaturated hydrocarbons or unsaturated hydrocarbons by themselves which are utilized as a starting material in the process of the present invention would include, in particular, monoolefinic hydrocarbons such as 1-butene, 2-butene, isobutylene, 1-pentene, 2-pentene, 2-methyl-1-pentene, 2-methyl-2-pentene, 1-heptene, 2-heptene, 3-heptene, 2-methyl-2-hexene, 3-methyl-2-hexene, 1-octene, 2-octene, 3-octene, 4-octene, 3-methyl-1-heptene, 2-methyl-2-heptene, 1-nonene, 2-nonene, 3-nonene, 4-nenene, 3-methyl-2-octene, 1-decene, 2-decene, 3-decene, 4-decene, 5-decene, 3,4-dimethyl-3-octene, 4-ethyl-2-octene, 1-undecene, 2-undecene, 3-undecene, 4-undecene, 5-undecene, 1-dodecene, 2-dodecene, 3-dodecene, 4-dodecene, 5-dodecene, 6-dodecene, 1-tridecene, 2-tridecene, 7-tetradecene, 3-pentadecene, 5-pentadecene, 6-pentadecene, 1-hexadecene, 6-heptadecene, etc.; or mixtures of internal and terminal olefins possessing carbon numbers ranging from 11 to 14, 15, to 18 and 18 to 21. It is also contemplated within the scope of this invention that dienic hydrocarbons (alkadienes and cycloalkadienes) may also be included within the term unsaturated hydrocarbon, the compounds giving results which are not necessarily equivalent to those obtained with mono-unsaturated hydrocarbons. The dienes are exemplified by 1,4-nonadiene, 1,7-octadiene, 1,3-heptadiene, 1,2-hexadiene, 1,5-hexadiene, 1,3-pentadiene, 1,4-cyclohexadiene, 1,5-cyclooctadiene, etc. In general, non-conjugated dienes are preferred over conjugated dienes.

It is contemplated within the scope of this invention that the catalyst comprising hydrogen fluoride may be present in either a liquid or a vapor phase to effect the carboxylation. As hereinbefore set forth, the novelty of the process of this invention concerns the presence of a promoter comprising a cuprous-containing compound. The addition of the cuprous-containing compound as an additive to the carboxylation process of the present invention results in the ability to use lower carbon monoxide pressures and still obtain good yields of carboxylic acid product. The most generally suitable example for cuprous-containing compound which may be utilized as a promoter of the present invention is cuprous oxide. Other cuprous-containing compounds which may be used within the scope of this invention are cuprous sulfate, cuprous chloride, cuprous iodide and cuprous acetate, although not necessarily with equivalent results; cuprous fluoride may also be used, but is not readily available. It should be noted that cuprous-containing compounds may occasionally be formed from cupric-containing compounds by reduction reactions with components of the reaction mixture in situ.

It is contemplated within the scope of this invention that the reaction may be effected in a medium which will comprise an inert organic compound. Suitable examples of inert organic mediums would comprise n-pentane, n-hexane, n-heptane, isooctane (2,2,4-trimethylpentane), benzene, toluene, pseudocumene, cyclopentane, cyclohexane, cycloheptane, etc. It is understood that the aforementioned unsaturated hydrocarbons, cuprous-containing compounds and inert organic medias are only representative of the class of compounds which may be employed, and that the present invention is not necessarily limited thereto.

The process of this invention may be effected in any suitable manner and may comprise either a batch or a continuous type operation. For example, when a batch type operation is employed, the cuprous compound and water are sealed in an appropriate apparatus, such as an autoclave or turbomixer; the hydrogen fluoride catalyst is pressed in after which the reactor is pressured with carbon monoxide until the desired operating pressure is maintained. The apparatus is then heated to the predetermined desired operating temperature and the unsaturated hydrocarbon is gradually added. The reactor is maintained at the reaction temperature for a predetermined residence time. At the end of this time, heating is discontinued, the autoclave is allowed to return to room temperature and the excess pressure is discharged by a venting procedure. The autoclave is opened and the reaction mixture is then treated in a manner (usually washing with water and extraction with ether or pentane) whereby the desired product, namely, the carboxylic acid, is recovered and separated from the catalyst, the promoter, and any unreacted starting materials and subjected to conventional means of purification and separation, said means includes washing, drying, extraction, fractional distillation, evaporation, etc. It is also contemplated within the batch type operation that atmospheric pressure may also be used. when atmospheric pressure is used, it is contemplated that the carbon monoxide may enter through the bottom of the reaction vessel to be bubbled through the reaction media to the surface.

It is also contemplated within the scope of this invention that the reaction process for obtaining the carboxylic acids may be effected in a continuous manner of operation. When such a type of operation is employed, unsaturated hydrocarbon, the carbon monoxide and the hydrogen fluoride plus the water are continuously charged to the reaction zone containing the cuprous-containing compound through separate lines. Alternatively, the cuprous-containing compound may be charged continuously to the reactor together with the hydrogen fluoride and the water. The reaction zone is maintained at proper operating conditions of temperature and pressure. After completion of the desired residence time the reactor effluent is continuously withdrawn and subjected to conventional means of separation whereby the desired carboxylic acid is recovered, while any unreacted starting materials comprising the carbon monoxide or the unsaturated hydrocarbon, and catalyst are recycled to the reaction zone to form a portion of the feed stock while any recovered cuprous-containing compound is recycled to the reaction zone.

Examples of suitable carboxylic acids which may be prepared according to the process of this invention will include all acids where the carboxylic acid moiety may be attached to any portion of the chain of carbon atoms such as all pentanoic acids, all hexanoic acids, all heptanoic acids, all octanoic acids, all nonanoic acids, all decanoic acids, all undecanoic acids, all dodecanoic acids, all tetradecanoic acids, all pentadecanoic acids, all hexadecanoic acids, all heptadecanoic acids, all octadecanoic acids, all eicosanoic acids, all tetracoscananoic acids, all hexenoic acids, all cyclohexenoic acids, all cyclooctenoic acids, etc.

The following examples are given to illustrate the process of the present invention which, however, are not intended to limit the generally broad scope of the present invention in strict accordance therewith.

EXAMPLE I

In this example 0.33 moles of water and 0.1 moles of cuprous oxide were charged to a 1 liter stainless steel turbomixer at room temperature. The turbomixer was cooled to a temperature of 0° C. by means of an ice bath, at which temperature 11.0 moles of hydrogen fluoride were charged to said turbomixer. Carbon monoxide was charged until the pressure in the turbomixer stabilized, said stabilization being caused by the termination of carbon monoxide absorption by the cuprous oxide. The pressure in the turbomixer was raised to 85 psi. Subsequently, 0.2 moles of 7-tetradecene was charged from a calibrated Jerguson gauge charger to the turbomixer over a period of time comprising 20 minutes. The turbomixer was stirred and heated to a temperature of 25°-30° C. while being maintained at a pressure of 85 psi with carbon monoxide. Stirring was continued for 37 minutes, after which the pressure was 50 psi. The turbomixer was vented thereby allowing it to return to ambient pressure and the turbomixer was emptied through a Kel-F-lined Jerguson gauge. The product phase was separated by physical means and analyzed by means of gas-liquid chromatography; said analysis disclosed the product to be pentadecanoic acids in a recovery of 75 mole percent.

EXAMPLE II

In this example 0.33 moles of water and 0.1 moles of cuprous oxide were sealed in a 1 liter stainless steel stirred turbomixer at room temperature. Eleven moles (11.0) of hydrogen fluoride was charged to the turbomixer and subsequently carbon monoxide was pressed into the turbomixer until the pressure stabilized, indicating complete carbon monoxide absorption by the cuprous oxide. After complete absorption, the turbomixer was cooled to 0° C. by means of an ice bath and the pressure was slowly released until the gauge recorded that the pressure dropped below 25 psi. The turbomixer was then rewarmed to 25° C. and maintained between 25° and 32° C. during an interval comprising 40 minutes during which 0.2 mole of 7-tetradecene was added; stirring was continued for an additional 16 minutes after which the turbomixer was vented, thereby allowing it to return to ambient pressure, and emptied through a Kel-F-lined Jerguson gauge. The product phase was separated by physical means and analyzed by means of gas-liquid chromatography, said analysis disclosing the product to be pentadecanoic acids in a recovery of 76 mole percent.

When the above experiment was repeated in the absence of any added cuprous oxide, the pressure of carbon monoxide which was required to obtain high yields of pentadecanoic acids was 330 psi. This contrasted with the pressures of 25 psi and 85 psi which were used to obtain the high yields of pentadecanoic acids when 0.1 moles of cuprous oxide was present in the reaction mixture.

EXAMPLE III

In this example 3.0 moles of water, 5.0 moles of n-pentane and 2.0 moles of cuprous oxide are charged to a rotating autoclave which is then sealed, 20.0 moles of hydrogen fluoride is added and carbon monoxide is pressed in until a stabilized pressure of 75 psi is obtained within the autoclave. The autoclave is heated to a temperature of 25° C. and maintained thereat for a period of time comprising 1 hour during which 2.0 moles of 2-nonene are added. After the 1-hour period of time, the autoclave is vented thereby allowing the return to ambient pressure and the heat is terminated thereby allowing the return to room temperature. The product is removed from the autoclave and separated from any unreacted material or catalyst and analyzed by means of gas-liquid chromatography, the analysis disclosing the product to be a mixtue of decanoic acids.

EXAMPLE IV

In this example, 5.0 moles of water, 3.0 moles of benzene and 2.5 moles of cuprous acetate are charged to a rotating autoclave, 25.0 moles of hydrogen fluoride and carbon monoxide is pressed in until a stabilized pressure of 100 psi is obtained within the autoclave. The autoclave is cooled to a temperature of 0° C. and maintained thereat for a period of time comprising 1 hour by means of an ice bath while 2.5 moles of 1-pentene are added. After the 1 hour period of time, the autoclave is vented thereby allowing the return to ambient pressure and the ice bath is removed thereby allowing the return to room temperature. The product is removed from the autoclave and separated from any unreacted material or catalyst and analyzed by means of gas-liquid chromatography, the analysis disclosing the product to consist chiefly of hexanoic acids.

EXAMPLE V

In this example 4.0 moles of water, 3.0 moles of pseudocumene, and 1.5 moles of cuprous oxide are charged to a rotating autoclave after which 25.0 moles of hydrogen fluoride and 50 psi of carbon monoxide (stabilized pressure) is added by the procedure described in the earlier examples. The autoclave is maintained at a temperature of 28°-30° C. for 2 hours, during which 1.5 moles of 5-decene are added. After additional stirring (30 minutes) the autoclave is vented thereby allowing the pressure to return to ambient pressure. The product is removed from the autoclave, separated from any unreacted material and catalyst, and analyzed by means of gas-liquid chromatography, the analysis disclosing the product to consist chiefly of undecanoic acids.

EXAMPLE VI

In this example 5.0 moles of water and 2.0 moles of cuprous chloride are charged to a rotating autoclave containing 21.0 moles of hydrogen fluoride. The autoclave is cooled to −5° C., sealed, and carbon monoxide is pressed in until the stable pressure of 40 psi is maintained within the autoclave. 1,4-Cyclohexadiene (1.2 moles) is added during 25 minutes with stirring and the autoclave is maintained at −5° C. for an additional 30 minutes. The autoclave is then vented, thereby allowing the autoclave to return to ambient pressure, and the autoclave is allowed to come to room temperature. The product is removed from the autoclave and separated from any unreacted material or catalyst and analyzed by means of gas-liquid chromatography, the analysis disclosing the product to comprise cyclohexenecarboxylic acids.

We claim as our invention:

1. In a process for the production of a carboxylic acid which comprises reacting a monoolefinic or diolefinic hydrocarbon with water and carbon monoxide in contact with a hydrogen fluoride catalyst, the improvement which comprises effecting the reaction in the presence of a promoter amount of a cuprous compound selected from the group consisting of cuprous oxide, sulfate, chloride, iodide, fluoride and acetate. pressure of about 25 p.s.i. to about 85 p.s.i. at a pressure of about 25 p.s.i. to about 85 p.s.i.

2. The process of claim 1 further characterized in that said reaction is effected at a temperature in the range of from about −10° to about 50° C.

3. The process of claim 1 further characterized in that said water is present in a molar ratio of from about 1.05 to about 10 moles of water per mole of said hydrocarbon.

4. The process of claim 1 further characterized in that said cuprous compound is cuprous oxide.

5. The process of claim 1 further characterized in that said cuprous compound is cuprous chloride.

6. The process of claim 1 further characterized in that said monoolefinic hydrocarbon is 7-tetradecene and said carboxylic acid is pentadecanoic acid.

7. The process of claim 1 further characterized in that said monoolefinic hydrocarbon is 1-pentene and said carboxylic acid is hexanoic acid.

8. The process of claim 1 further characterized in that said monoolefinic hydrocarbon is 2-nonene and said carboxylic acid is decanoic acid.

9. The process of claim 1 further characterized in that said monoolefinic hydrocarbon is 5-decene and said carboxylic acid is undecanoic acid.

10. The process of claim 1 further characterized in that said diolefinic hydrocarbon is 1,4-dyclohexadiene and said carboxylic acid is cyclohexene carboxylic acid.

* * * * *